US008586365B2

(12) United States Patent
Wells et al.

(10) Patent No.: US 8,586,365 B2
(45) Date of Patent: Nov. 19, 2013

(54) METHODS FOR ANALYZING AND OPTIMIZING BIOFUEL COMPOSITIONS

(75) Inventors: Paul P. Wells, Mullica Hill, NJ (US); Mike T. Noorman, Cinnaminson, NJ (US); Donna I. Hoel, Gibbsboro, NJ (US); Jacob J. Habeeb, Westfield, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 437 days.

(21) Appl. No.: 12/963,663

(22) Filed: Dec. 9, 2010

(65) Prior Publication Data
US 2011/0138679 A1 Jun. 16, 2011

Related U.S. Application Data

(60) Provisional application No. 61/284,223, filed on Dec. 15, 2009.

(51) Int. Cl.
*G01N 33/22* (2006.01)

(52) U.S. Cl.
USPC .................. 436/55; 436/128; 44/385; 44/903

(58) Field of Classification Search
USPC .................. 422/62; 436/55, 128; 44/385, 903
See application file for complete search history.

(56) References Cited

U.S. PATENT DOCUMENTS

| 7,404,411 B2 | 7/2008 | Welch et al. |
| 2006/0213554 A1 | 9/2006 | Welch et al. |
| 2008/0172187 A1 | 7/2008 | Koehler et al. |
| 2008/0256848 A1 | 10/2008 | Brennan et al. |

FOREIGN PATENT DOCUMENTS

| WO | 2006/101653 A2 | 9/2006 |
| WO | 2008/045565 A1 | 4/2008 |
| WO | 2008/0455565 A1 | 4/2008 |
| WO | 2008/080113 A2 | 7/2008 |

OTHER PUBLICATIONS

Giordani, D. S., Siqueira, A. F., Silva, M.L.C.P., Oliveira, P. C., de Castro, H. F., "Identification of the Biodiesel Source Using an Electronic Nose", Energy & Fuels 2008, 22, pp. 2743-2747.
Eide, Ingvar, Zahlsen, Kolbjorn, "Chemical Fingerprinting of Biodiesel Using Electrospray Mass Spectrometry and Chemometrics: Chracterization, Discrimination, Identification, and Quantification in Petrodiesel", Energy & Fuels 2007, 21, pp. 3702-3708.
Adam, Frederick, Bertoncini, Fabrice, Coupard, Vincent, Charon, Nadege, Thiebaut, Didier, Espinat, Didier, Hennion, Marie-Claire, "Using Comprehensive two-dimensional gas chromatography for the analysis of oxygenates in middle distillates I. Determination of the nature of biodiesels blend in diesel fuel", Journal of Chromatography A, 1186 (2008) pp. 236-244.
Tiyapongpattana, Warawut, Wilairat, Prapin, Marriott, Philip J., "Characterization of biodiesel and biodiesel blends using comprehensive two-dimensional gas chromatography", J. Sep. Sci. 2008, 31, pp. 2640-2649.
Catharino, Rodrigo R., Milagre, Humberto M.S., Saraiva, Sergio A., Garcia, Camila M., Schuchardt, Ulf, Eberlin, Marcos N., "Biodiesel Typification and Quality Control by Direct Infusion Electrospray Ionization Mass Spectrometry Fingerprinting", Energy & Fuels 2007, 21, pp. 3698-3701.
Rajendra, Machavaram, Jena, Prakash Chandra, Raheman, Hifjur, "Prediction of optimized pretreatment process parameters for biodiesel production using ANN and GA", Fuel 88 (2009) pp. 868-875.
Saraf, S., Thomas, B., "Influence of Feedstock and Process Chemistry on Biodiesel Quality", Institution of Chemical Engineers 2007, vol. 85 (B5), pp. 360-364.
Baroutian, Saeid, Aroua, Mohamed Kheireddine, Raman, Abdul Aziz Abdul, Sulaiman, Nik Meriam Nik, "Prediction of Palm Oil-Based Methyl Ester Biodiesel Density Using Artificial Neural Networks", Journal of Applied Sciences 8 (10), pp. 1938-1943, 2008, ISSN 1812-5654.
Van Gerpen, J., Shanks, B., Pruszko, R. (Iowa State University), Clements, D. (Renewable Products Development Laboratory), Knothe, G. (USDA/NCAUR), "Biodiesel Analytical Methods", National Renewable Energy Laboratory (NREL/SR-510-36240), Aug. 2002-Jan. 2004.
Leliveld, R.G., van Dillen, A.J., Geus, J.W., Koningsberger, D.C., "Structure and Nature of the Active Sites in CoMo Hydrotreating Catalysts Conversion of Thiophene", Journal of Catalysis 175, pp. 108-116 (1998).
Rana, Mohan S., Ramirez, Jorge, Gutierrez-Alejandre, Aida, Ancheyta, Jorge, Cedeno, Luis, Maity, S.K., "Support effects in CoMo hydrodesulfurization catalysts prepared with EDTA as a chelating agent", Journal of Catalysis 246 pp. 100-108 (2007).
Topsoe, Henrik, Clausen, Bjerne S., "Active Sites and Support Effects in Hydrodesulfurization Catalysts", Applied Catalysis, 25, pp. 273-293 (1986).
Roberts, C.D., "Improve sulfiding of hydroprocessing catalysts", An alternative safer, easier method to activate catalysts, Special Report, Hydrocarbon Processing, Sep. 2008.
Bamgboye, A.I.; Hansen, A.C.; "Prediction of cetane number of biodiesel fuel from the fatty acid methyl ester (FAME) composition", Institute of Agrophysics, Polish Academy of Sciences, 2008, 22, pp. 21-29.

*Primary Examiner* — Jan Ludlow

(74) *Attorney, Agent, or Firm* — Bradley A. Keller; David M. Weisberg (57) ABSTRACT

The invention provides novel methods for optimizing the design of a fatty acid alkyl ester-containing biofuel (e.g. a biodiesel, a biodiesel blend, or a jet biofuel) and for identifying a fatty acid alkyl ester-containing biofuel's feedstock.

20 Claims, 6 Drawing Sheets

| Property | Method | Base Diesel 03-57259 | | | Specifications D975 (S15) | EN 590 (1) |
|---|---|---|---|---|---|---|
| Flash Point, °C | D93 | 66.0 | | | 52 min | 55 min |
| Distillation, °C | D86 | | | | | |
| IBP | | 193.9 | 195.3 | 195.3 | | |
| 5 vol% recovered | | 209.3 | 210.6 | 209.6 | | |
| 10 vol% recovered | | 213.1 | 213.8 | 213.9 | | |
| 20 vol% recovered | | 221.5 | 222.6 | 222.7 | | |
| 30 vol% recovered | | 229.7 | 231.2 | 231 | | |
| 40 vol% recovered | | 237.8 | 238.6 | 238.7 | | |
| 50 vol% recovered | | 244.2 | 245 | 244.6 | | 65% max @ 250C |
| 60 vol% recovered | | 249.4 | 250.2 | 249.7 | | |
| 70 vol% recovered | | 255.9 | 256.9 | 255.8 | | |
| 80 vol% recovered | | 266.9 | 269.1 | 265.2 | | |
| 90 vol% recovered | | 308.1 | 309.2 | 299.8 | 282 - 338 | 85% min @ 350C |
| 95 vol% recovered | | 342.5 | 343 | 339.3 | | 360 max |
| END | | 350.9 | 346.4 | 349.8 | | |
| Vol % Recovered | | 97.9 | 97.2 | 98.1 | | |
| Kinematic Viscosity @ 40°C, mm²/s | D445 | 2.02 | | | 1.9 - 4.1 | 2.00 - 4.50 |
| Ash, wt% | D482 | <0.001 | | | 0.01 max | 0.01 max |
| Sulfur, mg/kg | D5453 | 13 | | | 15 max | 10.0 max |
| | D2622 | 11 | | | | |
| Cu Corrosion (3 hrs @ 50°C) | D130 | 1A | | | No. 3 max | class 1 |
| NACE Rust | | C | | | | |
| Cetane Number | D613 | 47.7 | | | 40 min | 51.0 min |
| Derived Cetane Number | D6890 | 46.8 | | | | |
| Cetane Index | D976 | 45.0 | | | 40 min | 46.0 min |
| Hydrocarbon Type, vol% | D1319 | | | | | |
| aromatics | | 30.59 | | | 35 max | |
| olefins | | 1.93 | | | | |
| saturates | | 67.49 | | | | |
| Aromatics Type, wt% | D5186 | | | | | |
| mono | | 23.1 | | | | |
| polynuclear | | 11.7 | | | | 11 max |
| total | | 34.8 | | | | |
| Cloud Point, °C | D5773 | -21.9 | -22.3 | | | |
| | D2500 | -24 | -22 | | | |
| Pour Point, °C | D5949 | -28 | | | | |
| | D5950 | -21 | -23 | | | |
| CFPP, °C | D6371 | -26 | | | | |
| LTFT, °C | D4539 | -22 | | | | |
| HFRR @ 15.6°C, μm | D6079 | 618 | | | 520 max | 460 max |
| Density @ 15°C, g/cm3 | D4052 | 0.8397 | | | | |
| Density @ 15.6°C, g/cm3 | D4052 | 0.8388 | | | | |
| Density @ 20°C, g/cm3 | D4052 | 0.8356 | | | | |
| Nitrogen, mg/kg | M1208 | 6.0 | | | | |
| Hydrogen Fraction, wt% | M1252 | 12.99 | | | | |
| Heat of Combustion | D4809 | | | | | |
| gross | | 45.5 | | | | |
| net | | 42.8 | | | | |
| C, H and N, wt% | D5291 | | | | | |
| carbon | | 85.91 | | | | |
| hydrogen | | 11.75 | | | | |
| nitrogen | | <0.75 | | | | |

Notes: (1) See EN 590 specification for appropriate test methods

Figure 3b

| Code # | | 07-27972 | 07-42280 | 07-17495 | 07-14905 |
|---|---|---|---|---|---|
| Biodiesel Type | | SME | RME | PME | TME |
| Compound, wt% | | | | | |
| Methyl butyrate | C4:0 | 0 | 0 | 0 | 0 |
| Methyl caproate | C6:0 | 0 | 0 | 0 | 0 |
| Methyl caprylate | C8:0 | 0 | 0 | 0 | 0 |
| Methyl caprate | C10:0 | 0 | 0 | 0 | 0 |
| Methyl undecanoate | C11:0 | 0 | 0 | 0 | 0 |
| Methyl laurate | C12:0 | 0 | 0 | 0.34 | 0.09 |
| Methyl tridecanoate | C13:0 | 0 | 0 | 0 | 0 |
| Methyl myristate | C14:0 | 0 | 0 | 0.97 | 1.44 |
| Methyl myristoleate | C14:1 cis-9 | 0 | 0 | 0 | 0 |
| Methyl pentadecanoate | C15:0 | 0 | 0 | 0 | 0 |
| Methyl-pentadecenoate | C15:1 cis-10 | 0 | 0 | 0 | 0 |
| Methyl palmitate | C16:0 | 10.76 | 5.41 | 43.29 | 23.85 |
| Methyl palmitoleate | C16:1 cis-9 | 0.11 | 0.22 | 0.16 | 2.63 |
| Methyl heptadecanoate | C17:0 | 0 | 0 | 0 | 0.35 |
| Methyl heptadecenoate | C17:1 cis-10 | 0 | 0 | 0 | 0.34 |
| Methyl stearate | C18:0 | 4.14 | 2.11 | 4.52 | 11.72 |
| Methyl oleate | C18:1 cis-9 | 21.25 | 54.27 | 37.27 | 41.15 |
| Methyl elaidate | C18:1 trans-9 | 1.47 | 3.41 | 0.72 | 3.23 |
| Methyl linoleate | C18:2 cis-9,12 | 54.02 | 25.16 | 9.78 | 13.3 |
| Methyl g-linolenate | C18:3 cis-9,12,15 | 7.72 | 8.31 | 0 | 0 |
| Methyl a-linolenate | C18:3 cis-9,12,15 | 0.21 | 0 | 0.21 | 0.84 |
| Methyl arachidate | C20:0 | 0.13 | 0.70 | 0.35 | 0.19 |
| Methyl-eicosenoate | C20:1 cis-11 | 0 | 0 | 0.12 | 0.73 |
| Methyl eicosadienoate | C20:2 cis-11,14 | 0 | 0 | 0 | 0.42 |
| Methyl eicostrenoate | C20:3 cis-8,11,14 | 0 | 0 | 0 | 0 |
| Methyl henicosanoate | C21:0 | 0 | 0 | 0 | 0 |
| Methyl eicosatrienoate | C20:3 cis-11,14,17 | 0 | 0 | 0 | 0 |
| Methyl arachidonoate | C20:4 cis- 5,8,11,14 | 0 | 0 | 0 | 0 |
| cis--5,8,11,14,17-eicos | C20:5 cis-5,8,11,14,17 | 0 | 0 | 0 | 0 |
| Methyl behenate | C22:0 | 0 | 0 | 0 | 0 |
| Methyl erucate | C22:1 cis-13 | 0 | 0 | 0 | 0 |
| Methyl docosadienoate | C22:2 cis-13,16 | 0 | 0 | 0 | 0 |
| Methyl tricosanoate | C23:0 | 0 | 0 | 0 | 0 |
| Methyl lignocerate | C24:0 | 0 | 0 | 0 | 0 |
| cis-4,7,10,13,16,19- | C22:6 cis-4,7,10,13,16,19 | 0 | 0 | 0 | 0 |
| Methyl nervonate | C24:1 cis-15 | 0 | 0 | 0 | 0 |
| Other | | 1.2 | 2.51 | 0.41 | 0.95 |
| Total (+/- 3%) | | 101 | 102.10 | 98.14 | 101.23 |

Figure 3c

| Raw GC Data | | 07-27972 | 07-42280 | 07-17495 | 07-14905 | |
|---|---|---|---|---|---|---|
| Methyl caprylate | C8:0 | 0.00 | 0.00 | 0.00 | 0.00 | 0.00 |
| Methyl caprate | C10:0 | 0.00 | 0.00 | 0.00 | 0.00 | 0.00 |
| Methyl laurate | C12:0 | 0.00 | 0.00 | 0.34 | 0.09 | 0.00 |
| Methyl myristate | C14:0 | 0.00 | 0.00 | 0.97 | 1.44 | 0.00 |
| Methyl palmitate | C16:0 | 10.76 | 5.41 | 43.29 | 23.85 | 0.00 |
| Methyl palmitoleate | C16:1 cis-9 | 0.11 | 0.22 | 0.16 | 2.63 | 0.00 |
| Methyl heptadecanoate | C17:0 | 0.00 | 0.00 | 0.00 | 0.35 | 0.00 |
| Methyl stearate | C18:0 | 4.14 | 2.11 | 4.52 | 11.72 | 0.00 |
| Methyl oleate | C18:1 cis-9 | 21.25 | 54.27 | 37.27 | 41.15 | 0.00 |
| Methyl elaidate | C18:1 trans-9 | 1.47 | 3.41 | 0.72 | 3.23 | 0.00 |
| Methyl linoleate | C18:2 cis-9,12 | 54.02 | 25.16 | 9.78 | 13.30 | 0.00 |
| Methyl linolenate | C18:3 cis-9,12,15 | 7.93 | 8.31 | 0.21 | 0.84 | 0.00 |
| Methyl arachidate | C20:0 | 0.13 | 0.70 | 0.35 | 0.19 | 0.00 |
| Total | Recovery | 99.81 | 99.59 | 97.61 | 98.79 | 0.00 |
| Normalized GC Data | | | | | | |
| Methyl caprylate | C8:0 | 0.00 | 0.00 | 0.00 | 0.00 | #DIV/0! |
| Methyl caprate | C10:0 | 0.00 | 0.00 | 0.00 | 0.00 | #DIV/0! |
| Methyl laurate | C12:0 | 0.00 | 0.00 | 0.35 | 0.09 | #DIV/0! |
| Methyl myristate | C14:0 | 0.00 | 0.00 | 0.99 | 1.46 | #DIV/0! |
| Methyl palmitate | C16:0 | 10.78 | 5.43 | 44.35 | 24.14 | #DIV/0! |
| Methyl palmitoleate | C16:1 cis-9 | 0.11 | 0.22 | 0.16 | 2.66 | #DIV/0! |
| Methyl heptadecanoate | C17:0 | 0.00 | 0.00 | 0.00 | 0.35 | #DIV/0! |
| Methyl stearate | C18:0 | 4.15 | 2.12 | 4.63 | 11.86 | #DIV/0! |
| Methyl oleate | C18:1 cis-9 | 21.29 | 54.49 | 38.18 | 41.65 | #DIV/0! |
| Methyl elaidate | C18:1 trans-9 | 1.47 | 3.42 | 0.74 | 3.27 | #DIV/0! |
| Methyl linoleate | C18:2 cis-9,12 | 54.12 | 25.26 | 10.02 | 13.46 | #DIV/0! |
| Methyl linolenate | C18:3 cis-9,12,15 | 7.95 | 8.34 | 0.22 | 0.85 | #DIV/0! |
| Methyl arachidate | C20:0 | 0.13 | 0.70 | 0.36 | 0.19 | #DIV/0! |
| Total | Recovery | 100.00 | 100.00 | 100.00 | 100.00 | #DIV/0! |
| | monounsaturates | 22.87 | 58.14 | 39.08 | 47.59 | #DIV/0! |
| | polyunsaturates | 62.07 | 33.61 | 10.23 | 14.31 | #DIV/0! |
| | saturates | 15.06 | 8.25 | 50.68 | 38.10 | #DIV/0! |
| Rapeseed Methyl Ester Calculation | | | | | | |
| | C18:1 cis-9 to saturates | 1.41384 | 6.60219 | 0.75339 | 1.09325 | #DIV/0! |
| | C18:1 cis-9 to C18:0 | 5.13285 | 25.72038 | 8.24558 | 3.51109 | #DIV/0! |
| | Calc., fct. (raw) | 0.06 | 0.85 | 0.06 | 0.00 | #DIV/0! |
| | Convert negatives to zero | 0.06 | 0.85 | 0.06 | 0.00 | #DIV/0! |
| | Calc., fct. (normalized) | 0.05 | 0.89 | 0.07 | 0.00 | #DIV/0! |
| Soybean Methyl Ester Calculation | | | | | | |
| | C18:2 cis-9,12 to C18:1 cis-9 | 2.54212 | 0.46361 | 0.26241 | 0.32321 | #DIV/0! |
| | Calc., fct. (raw) | 1.08 | 0.09 | -0.01 | 0.02 | #DIV/0! |
| | Convert negatives to zero | 1.08 | 0.09 | 0.00 | 0.02 | #DIV/0! |
| | Calc., fct. (normalized) | 0.89 | 0.09 | 0.00 | 0.02 | #DIV/0! |
| Palm Oil Methyl Ester Calculation | | | | | | |
| | C16:0 | 10.78 | 5.43 | 44.35 | 24.14 | #DIV/0! |
| | C16:0 to C18:0 | 2.59903 | 2.56398 | 9.57743 | 2.03498 | #DIV/0! |
| | Calc., fct. (raw) | 0.04 | 0.01 | 0.85 | 0.05 | #DIV/0! |
| | Convert negatives to zero | 0.04 | 0.01 | 0.85 | 0.05 | #DIV/0! |
| | Calc., fct. (normalized) | 0.03 | 0.01 | 0.91 | 0.04 | #DIV/0! |
| Tallow Methyl Ester Calculation | | | | | | |
| | C16:1 cis-9 | 0.11 | 0.22 | 0.16 | 2.66 | #DIV/0! |
| | C16:1 cis-9 to C20:0 | 0.84615 | 0.31429 | 0.45714 | 13.84211 | #DIV/0! |
| | Calc., fct. (raw) | 0.00 | 0.01 | 0.00 | 1.08 | #DIV/0! |
| | Convert negatives to zero | 0.00 | 0.01 | 0.00 | 1.08 | #DIV/0! |
| | Calc., fct. (normalized) | 0.00 | 0.01 | 0.00 | 0.93 | #DIV/0! |
| Jatropha Methyl Ester Calculation | | | | | | |
| | C18:1 cis-9 to C18:3 cis-9,12,15 | 2.68 | 6.53 | 177.48 | 48.99 | #DIV/0! |
| | C18:2 cis-9,12 to C18:3 cis-9,12,15 | 6.81 | 3.03 | 46.57 | 15.83 | #DIV/0! |
| | polyunsaturates to C18:3 cis-9,12,15 | 7.81211 | 4.02768 | 47.57143 | 16.83333 | #DIV/0! |
| | Calc., fct. (raw) | 0.03 | -0.01 | 0.02 | 0.01 | #DIV/0! |
| | Convert negatives to zero | 0.03 | 0.00 | 0.02 | 0.01 | #DIV/0! |
| | Calc., fct. (normalized) | 0.02 | 0.00 | 0.02 | 0.01 | #DIV/0! |
| Coconut Methyl Ester Calculation | | | | | | |
| | C8:0 to C10:0 | 0.00 | 0.00 | 0.00 | 0.00 | #DIV/0! |
| | Calc., fct. (raw) | 0.00 | 0.00 | 0.00 | 0.00 | #DIV/0! |
| | Convert negatives to zero | 0.00 | 0.00 | 0.00 | 0.00 | #DIV/0! |
| | Calc., fct. (normalized) | 0.00 | 0.00 | 0.00 | 0.00 | #DIV/0! |
| | Sum (all methyl esters identified above) | 1.21 | 0.96 | 0.94 | 1.16 | #DIV/0! |

Figure 3d

| | |
|---|---|
| Code # | 03-57259 |
| Base Diesel, vol% | 100 |
| IQT (D6890), derived cetane number | 46.7 |
| | 47.8 |
| | 48.4 |
| | 47.8 |
| | 45.6 |
| | 45.6 |
| | 46.2 |
| | 46.5 |
| | 46.4 |
| IQT Run # | 1880, 2077, 2092, 2093, 2300, 2301, 2309, 2310, 2311 |
| IQT Average | 46.8 |
| | |
| Code # | 07-59710 |
| Base Diesel, vol% | 90 |
| SME, vol% | 10 |
| IQT (D6890), derived cetane number | 47.2 |
| IQT Run # | 1838 |
| | |
| Code # | 07-59715 |
| Base Diesel, vol% | 90 |
| RME, vol% | 10 |
| IQT (D6890), derived cetane number | 50.0 |
| IQT Run # | 1845 |
| | |
| Code # | 07-59747 |
| Base Diesel, vol% | 90 |
| PME, vol% | 10 |
| IQT (D6890), derived cetane number | 51.6 |
| IQT Run # | 1849 |
| | |
| Code # | 07-59755 |
| Base Diesel, vol% | 90 |
| TME, vol% | 10 |
| IQT (D6890), derived cetane number | 48.7 |
| IQT Run # | 1856 |

METHODS FOR ANALYZING AND OPTIMIZING BIOFUEL COMPOSITIONS

This Application claims the benefit of U.S. Application No. 61/284,223, filed Dec. 15, 2009.

FIELD OF THE INVENTION

The invention provides methods for analyzing and optimizing biofuel compositions.

BACKGROUND OF THE INVENTION

Biodiesel is the name for a variety of ester-based oxygenated fuels made from vegetable oils, fats, greases, or other sources of triglycerides. Biodiesel is a nontoxic and biodegradable blendstock which may be blended with petroleum diesel provided relevant specifications are met. Biodiesel has been designated as an alternative fuel by the United States Department of Energy and the United States Department of Transportation, and is registered with the United States Environmental Protection Agency as a fuel and fuel additive.

Because biodiesel is made from numerous different feedstocks (e.g. rapeseed oil and palm oil), including mixed feedstocks, a finished fuel manufacturer is often not aware of the exact feedstock composition of a purchased biodiesel. Biodiesel is commonly referred to by its feedstock source (e.g. rapeseed methyl ester, palm oil methyl ester). Since the performance of a biodiesel depends upon the particular feedstock mixture from which it was produced, formulators are therefore often unable to predict how the biodiesel will perform in the finished fuel blend. For example, in the absence of accurate feedstock information, it can prove difficult to anticipate whether any given biodiesel will afford a performance advantage such as an improved cetane number, or will in fact suffer from a performance disadvantage (such as poor low-temperature operability) that might call for the addition of a performance enhancer.

Lack of a reliable biodiesel compositional profile also complicates fuel formulators' efforts to design biodiesel blends that satisfy applicable regulatory standards such as ASTM D975, ASTM D7467 Standard Specification for Diesel Fuel Oil, Biodiesel Blend (B6-B20), and EN590. The performance criteria and characteristics mandated by such standards are linked inextricably with a biodiesel's composition.

Giordani, et al., "Identification of the Biodiesel Source Using an Electronic Nose", *Energy & Fuels* 2008, 22, 2743-2747, discloses the use of an e-nose and neural networks to identify a biodiesel feedstock source. Eide, et al. "Chemical Fingerprinting of Biodiesel Using Electrospray Mass Spectrometry and Chemometrics: Characterization, Discrimination, Identification, and Quantification in Petrodiesel, *Energy & Fuels* 2007, 21, 3702-3708, discloses the use of electrospray mass spectrometry (ESI-MS) to discriminate between biodiesel from different feedstocks and manufacturers, to identify fatty acid methyl esters (FAME) and free fatty acids, and to identify and quantify blend composition. Adam, et al., "Using comprehensive two-dimensional gas chromatography for the analysis of oxygenates in middle ditillates I. Determination of the nature of biodiesel blend in diesel fuel", *J. Chromatogr. A* 1186 (2008) 236-244, discloses the use of two-dimensional gas chromatography (GC×GC) to quantify fatty acid esters in middle distillate hydrocarbons and individual identification and quantitation of fatty acid acid ester blends with diesel. Catharino, et al., "Biodiesel Typification and Quality Control by Direct Infusion Electrospray Ionization Mass Spectrometry Fingerprinting", *Energy & Fuels* 2007, 21, 3698-3701, discloses the use of ESI-MS for fingerprinting and quality control of biodiesels. Tiyapongpattana, et al., "Characterization of biodiesel and biodiesel blends using comprehensive two-dimensional gas chromatography", *J. Sep. Sci.* 2008, 31, 2640-2649, discloses a 2-D gas chromatography flame ionization detection method for biodiesel fuels.

The techniques cited in the above references do not provide readily programmable algorithmic techniques that correlate biodiesel FAME composition and feedstock source, and therefore are not well-suited to control of biodiesel fuel blending.

Processes which seek to optimize fuel composition by analysis of the amount of biodiesel in a biodiesel blend, such as the processes described in U. S. Pat. No. 7,404,411, fail to address the formulation problems mentioned above because they merely quantify the amount of biodiesel and do not provide any pre-blending qualitative analysis of biodiesel feedstock.

Accordingly, the need exists for methods which will accurately and conveniently analyze fatty acid alkyl ester-containing biofuels such as biodiesel, which will enable fuel formulators to optimize the design of fatty acid alkyl ester-containing biofuels, and which will facilitate the identification of a fatty acid alkyl ester-containing biofuel's feedstock.

SUMMARY OF THE INVENTION

We have discovered novel methods for optimizing the design of fatty acid alkyl ester-containing biofuels (e.g. a biodiesel or biodiesel blend) and for identifying a fatty acid alkyl ester-containing biofuel's feedstock.

In one aspect, the methods described herein accurately and conveniently determine the volumetric percentages of fatty acid alkyl esters (e.g. rapeseed oil methyl ester (RME), soybean oil methyl ester (SME), palm oil methyl ester (PME), and tallow oil methyl ester (TME)) in a biodiesel or biodiesel component of a biodiesel blend and enable manufacturers to ascertain whether fuels made from the biodiesel or biodiesel blend will exhibit performance advantages (e.g. improved cetane number) or disadvantages (e.g. poor low temperature operability) that will influence finished fuel specifications.

In one aspect, the methods described herein optimize the composition of a fatty acid alkyl ester-containing biofuel (e.g. a biodiesel or biodiesel blend) and comprise:

(a) submitting a sample of a fatty acid alkyl ester-containing component of the biofuel to an analyzer which measures the mass percentages in the component of at least two fatty acid alkyl esters (e.g. methyl oleate);

(b) inputting values indicative of the at least two fatty acid alkyl ester mass percentages into a processor which, in accordance with preprogrammed instructions (1) calculates one or more fatty acid alkyl ester mass percentage ratios and algorithmically determines the volumetric percentages of one or more fatty acid alkyl esters (e.g. RME, SME, PME, TME) in the component using the one or more fatty acid alkyl ester mass percentage ratios as algorithmic independent variables (2) correlates the one or more fatty acid alkyl ester volumetric percentages to fuel performance data and generates an output signal indicative of that correlation; and (c) controlling blending of the biofuel in response to the processor output signal.

In another aspect, the methods described herein optimize the composition of a fatty acid alkyl ester-containing biofuel (e.g. a biodiesel or biodiesel blend) and comprise:

(a) submitting a sample of a fatty acid alkyl ester-containing component of the biofuel to an analyzer which measures the mass percentages in the component of at least two fatty acid alkyl esters;

(b) determining total mass percentages of saturated, monounsaturated, and polyunsaturated fatty acid alkyl esters in the component;

(c) inputting values indicative of (i) the at least two fatty acid alkyl ester mass percentages, and (ii) the total mass percentages of saturated, monounsaturated, and polyunsaturated fatty acid alkyl esters into a processor which, in accordance with preprogrammed instructions (1) calculates (i) one or more fatty acid alkyl ester mass percentage ratios (ii) ratios of the mass percentage of each of the at least two fatty acid alkyl esters and the total mass percentages of saturated, monounsaturated, and polyunsaturated fatty acid alkyl esters (2) algorithmically determines the volumetric percentages of one or more fatty acid alkyl esters in the component using the one or more fatty acid alkyl ester mass percentage ratios, the total mass percentages of saturated, monounsaturated, and polyunsaturated fatty acid alkyl esters, and the ratios of the mass percentage of each of the at least two fatty acid alkyl esters and the total mass percentages of saturated, monounsaturated, and polyunsaturated fatty acid alkyl esters as algorithmic independent variables (4) correlates the one or more fatty acid alkyl ester volumetric percentages to fuel performance data and generates an output signal indicative of that correlation; and (d) controlling blending of the biofuel in response to the processor output signal.

In certain aspects, the analyzer or the processor determines the total mass percentages of saturated, monounsaturated, and polyunsaturated fatty acid alkyl esters present in the component. In certain aspects, the processor is a component of the analyzer.

In one aspect, the processor calculates four or more fatty acid alkyl ester mass percentage ratios and algorithmically determines the volumetric percentages of four or more fatty acid alkyl esters in the fatty acid alkyl ester-containing component.

In certain aspects, the biofuel is a biodiesel or a biodiesel blend, fatty acid alkyl ester volumetric percentages are correlated to reference biodiesel feedstock triglyceride (free fatty acid) profiles, and the feedstock of the biodiesel is thereby determined.

In certain aspects, the processor is a neural network which uses associative memory to generate algorithms that determine the volumetric percentages of the fatty acid alkyl esters.

In certain aspects, the analyzer measures the mass percentages in a biodiesel or a biodiesel component of a biodiesel blend of at least four alkyl esters of fatty acids selected from the group consisting of myristic acid (C14:0), palmitic acid (C16:0), palmitoleic acid (C16:1), stearic acid (C18:0), oleic acid (C18:1), linoleic acid (C18:2), linolenic acid (C18:3), eicosanoic acid (C20:0), eicosenoic acid (C20:1), docosanoic acid (C22:0), and docosenoic acid (C22:1).

In certain aspects, the processor determines the volumetric percentage in a biodiesel or a biodiesel component of a biodiesel blend of one or more compositions selected from the group consisting of soybean oil alkyl ester, rapeseed oil alkyl ester, palm oil alkyl ester, canola oil alkyl ester, sunflower oil alkyl ester, olive oil alkyl ester, corn oil alkyl ester, tallow oil alkyl ester, coconut oil alkyl ester, jatropha oil alkyl ester, yellow grease alkyl ester, animal fat alkyl ester, used cooking oil alkyl ester, and mixtures thereof For example, in one aspect of the methods described herein:

(a) the analyzer measures the mass percentages in a biodiesel or a biodiesel component of a biodiesel blend of methyl esters of palmitic acid (C16:0), palmitoleic acid (C16:1), oleic acid (C18:1 cis 9) or oleic acid (C18:1 trans 9), and linoleic acid (C18:2 cis 9, 12);

(b) the processor calculates the following mass percentage ratios: (1) linoleic acid methyl ester: oleic acid methyl ester (2) oleic acid methyl ester: palmitic acid methyl ester (3) palmitoleic acid methyl ester: palmitic acid methyl ester, and (4) palmitic acid methyl ester: oleic acid methyl ester (5) the ratios of the mass percentages of each of the at least two fatty acid alkyl esters and the total mass percentages of saturated, monounsaturated, and polyunsaturated fatty acid alkyl esters; and (c) the processor determines the volumetric percentage in the biodiesel or biodiesel component of the biodiesel blend of soybean oil methyl ester (SME), rapeseed oil methyl ester (RME), tallow oil methyl ester (TME), palm oil methyl ester (PME), coconut oil methyl ester (CME), and jatropha oil methyl ester (JME) using either or both of the following two sets of algorithms:

Set 1
 (a) $SME=0.993*(C18:2 \text{ cis-}9, 12/C18:1 \text{ cis-}9)^{0.5}-0.520$
 (b) $RME=0.089*(C18:1 \text{ cis-}9/C16:0)-0.104$;
 (c) $TME=86.671*(C16:1 \text{ cis-}9/C16:0)^2-0.030$; and
 (d) $PME=0.018*(C16:0/C18:1 \text{ trans-}9)-0.069$ Set 2
 (a) $TME=-0.053+0.219*(C16:1 \text{ cis-}9)+0.039*(C16:1 \text{ cis-}9 \text{ to } C20:0)$
 (b) $RME=-0.149+0.079*(C18:1 \text{ cis-}9 \text{ to sats})+0.019*(C18:1 \text{ cis-}9 \text{ to } C18:0)$
 (c) $SME=-0.133+0.476*(C18:2 \text{ cis-}9,12 \text{ to } C18:1 \text{ cis-}9)$
 (d) $PME=-0.258+0.005*(C16:0)+0.094*(C16:0 \text{ to } C18:0)$
 (e) $CME=2.244E-8+0.835*(C8:0 \text{ to } C10:0)$
 (f) $JME=-2.034E-3*(C18:1 \text{ cis-}9 \text{ to } C18:3 \text{ cis-}9,12,15)+0.035*(C18:2 \text{ cis-}9,12 \text{ to } C18:3 \text{ cis-}9,12,15)-0.026*(\text{poly to } C18:3 \text{ cis-}9,12,15)$ Mass percentages may be determined by any number of techniques that are well-known to those of ordinary skill in the art, including gas chromatography and other techniques described hereinafter. As explained in more detail hereinafter, the algorithmic determination of the volumetric percentages of the various vegetable and animal alkyl esters may be based on a statistical correlation of the known fatty acid alkyl ester profiles of vegetable and animal oil fatty acid alkyl esters and the determined ratios of the mass percentages of alkyl esters of fatty acids.

Through use of the methods described herein, formulators are able to ascertain accurately how a particular fatty acid alkyl ester profile of a biofuel (e.g. a biodiesel or a biodiesel blend) will affect fuel performance and can thereby optimize fuel design by varying as necessary the biofuel feedstock source or blended fuel components. For example, by knowing the fatty acid alkyl ester profile of a biodiesel or biodiesel component of a biodiesel blend, a finished fuel manufacturer is better able to utilize any performance advantage (e.g. cetane number improvement) and/or counter any performance disadvantage (e.g. poor low temperature operability) through appropriate use of additive(s). By using the methods described herein, refiners are also able to confirm whether a biofuel's composition is consistent with specifications provided by the biofuel's supplier. They also can also employ optimal blending strategies (e.g. use of additives) that compensate for the use of more sustainable biomass (i.e. less food-source consuming) and/or less-expensive biofuel feedstock sources.

Methods described herein provide a very good agreement between predicted and the actual compositions and their speed and economy prove well-suited for refinery operation.

These and other aspects are described further in the following detailed description of the invention.

BRIEF DESCRIPTION OF THE FIGURES

FIGS. 3a, 3b, 3c and 3d present the fuel composition, fuel properties, and fuel fatty acid alkyl ester profile determined in Example 2. FIG. 3a presents the base diesel fuel properties determined in Example 2. FIG. 3b is the FAME Composition Calculator (fuel fatty acid alkyl ester profile) determined in Example 2. FIG. 3c is the GC analysis of biodiesel samples determined in Example 2.

DETAILED DESCRIPTION OF THE INVENTION

Unless otherwise stated, all percentages disclosed herein are on a volume basis.

Any end point of a range stated herein can be combined with any other end point to form another suitable range.

The following definitions apply unless indicated otherwise.

A "fatty acid alkyl ester-containing biofuel" includes any fuel comprised of fatty acid alky esters made by the transesterification of a triglyceride with an alcohol. Fatty acid alkyl ester-containing biofuels include, but are not limited to, a biodiesel, a biodiesel blend, and a jet biofuel comprised of fatty acid alky esters.

A "biodiesel" means a composition that can be used as a fuel for diesel engines and that contains at least about 50% by weight of esters of saturated and unsaturated fatty acids, including fatty acid methyl esters (FAME's), fatty acid ethyl esters (FAEE's), propyl esters of fatty acids, or combinations of two or more methyl, ethyl, and propyl esters. In one example, a biodiesel comprises between about 50% to about 99% by weight of methyl esters of saturated and unsaturated fatty acids, where the methyl esters of saturated and unsaturated fatty acids include $C_8$-$C_{24}$ fatty acid methyl esters, where $C_8$-$C_{24}$ indicates the number of carbons in the original fatty acid.

Biodiesels can be made by transesterification of a triglyceride-containing feedstock with an alcohol, e.g. by transesterification of one or more vegetable oils, animal fats, algae-derived triglycerides, oils from halophytes, or mixtures thereof (e.g. transesterification of soybean oil, rapeseed oil, palm oil, canola oil, sunflower oil, olive oil, corn oil, tallow oil, coconut oil, jatropha oil, yellow grease, animal fats, used cooking oil, and mixtures thereof) with an alcohol such as methanol or ethanol. In one aspect the fatty acid alkyl esters are largely unsaturated and comprise a rapeseed methyl ester, a canola methyl ester, a soybean methyl ester, a corn oil methyl ester, or a mixture thereof.

A 100% biodiesel (B100) should meet ASTM D6751 and/or EN 14214 or EN14213 specifications.

Biodiesels can contain alkyl esters (e.g. methyl esters) of fatty acids such as myristic acid (C14:0), palmitic acid (C16:0), palmitoleic acid (C16:1), stearic acid (C18:0), oleic acid (C18:1), linoleic acid (C18:2), linolenic acid (C18:3), eicosanoic acid (C20:0), eicosenoic acid (C20:1), docosanoic acid (C22:0), and docosenoic (or erucic) acid (C22:1). The fuel properties of biodiesel are determined by the amounts of each fatty acid in the feedstock used to produce the esters. Fatty acids are designated by two numbers: the first number denotes the total number of carbon atoms in the fatty acid chain and the second is the number of double bonds present in the chain. For example, 18:1 designates oleic acid, which has 18 carbon atoms and one double bond.

The triglyceride or free fatty acid profiles of a number of common vegetable oils and animal fats are known. See e.g. Peterson, C. L., "Vegetable Oil as a Diesel Fuel: Status and Research Priorities," ASAE Transactions, V. 29, No. 5, Sep.-Oct. 1986, pp. 1413-1422.

As explained above, in certain aspects of the invention, the biofuel is a biodiesel or a biodiesel blend, fatty acid alkyl ester volumetric percentages are correlated to reference biodiesel feedstock triglyceride profiles, and the feedstock of the biodiesel is thereby determined. For example, fatty acid alkyl ester volumetric percentages are compared to known biodiesel feedstock triglyceride (free fatty acid) profiles such as those described in Catharino, et al., *Energy & Fuels* 2007, 21, p. 3700, Table 1) and the biodiesel feedstock is identified.

Biodiesel blends (biodiesel blended with a petroleum distillate such as diesel fuel)(Bx)) have a composition reflective of blend ratio and the distillate chosen for the blend.

"Petroleum distillate" includes naphtha or middle distillates including kerosene and diesel.

A non-limiting example of a "diesel fuel" or "a diesel" is composed of a mixture of $C_9$-$C_{24}$ hydrocarbons that comprise about 50% to about 95% by volume of aliphatic hydrocarbons, of which about 0% to about 50% by volume are cycloparaffins, about 0% to about 5% by volume of olefinic hydrocarbons, and about 5% to about 50% by volume of aromatic hydrocarbons, and which boil at between about 280° F. (138° C.) and 750° F. (399° C.).

A non-limiting example of a "kerosene" comprises about 5% to about 50% by volume of an aromatic fraction, about 0% to about 50% by volume of a cycloparaffin fraction, and about 0% to about 5% by volume of an olefinic fraction, with the rest comprising aliphatic hydrocarbons.

An aromatics fraction can contain methyl aromatics and non-methyl alkyl aromatics. Non-limiting examples of non-methyl alkyl aromatics include molecules such as alkyl benzenes, dialkylbenzenes, alkylnaphthalenes, alkyl biphenyls, and alkyl phenanthrenes, and the like, in which one or more linear or branched alkyl groups containing two or more carbons is bonded to the aromatic ring. Non-limiting examples of methyl aromatics include aromatic molecules such as methylnaphthalene, dimethylnaphthalenes, and the like.

A cycloparaffin fraction consists of cycloalkanes or molecules containing at least one cycloalkane ring. Non-limiting examples of components of the cycloparaffin fraction include alkylcyclohexanes and alkylcyclopentanes.

An olefinic fraction can contain linear, branched, and cyclo-olefins. Non-limiting examples of components of the olefinic fraction include dodecenes and hexadecenes.

A "cetane improver" includes but is not limited to 2-ethylhexyl nitrate (EHN) (e.g. HITEC® 4103, Ethyl Corp., Richmond, Va.), cyclohexyl nitrate, di-tert-butyl peroxide, methyl nitrate, ethyl nitrate, n-propyl nitrate, isopropyl nitrate, allyl nitrate, n-butyl nitrate, isobutyl nitrate, sec-butyl nitrate, tert-butyl nitrate, n-amyl nitrate, isoamyl nitrate, 2-amyl nitrate, 3-amyl nitrate, tert-amyl nitrate, n-hexyl nitrate, 2-ethylhexyl nitrate, n-heptyl nitrate, sec-heptyl nitrate, n-octyl nitrate, sec-octyl nitrate, n-nonyl nitrate, n-decyl nitrate, n-dodecyl nitrate, cyclopentylnitrate, cyclohexylnitrate, methylcyclohexyl nitrate, isopropylcyclohexyl nitrate, and the esters of alkoxy substituted aliphatic alcohols, such as 1-methoxypropyl-2-nitrate, 1-ethoxypropyl-2 nitrate, 1-isopropoxy-butyl nitrate, 1-ethoxylbutyl nitrate, and mixtures thereof In one aspect, a biodiesel or biodiesel blend may also include an aromatic amine antioxidant (e.g. a phenylediamine-type antioxidant) such as N, N'-di-sec-butyl-p-phenylenediamine, 4-isopropylaminodiphenylamine, phenylnaphthyl amine, and ring-alkylated diphenylamines.

A fatty acid alkyl ester-containing biofuel such as a biodiesel or biodiesel blend may also include performance additives such as cold flow additives, cloud point depressants, biocides, conductivity improvers, corrosion inhibitors, metal deactivators, and engine cleaning agents. In some aspects, such additives are present in an amount which ranges from about 0.001 to about 2.0% by weight of the fuel composition.

"Fuel performance data" includes, but is not limited to, values indicative of lubricity, specific gravity, kinematic viscosity, flash point, boiling point, cetane number, cloud point, pour point, lubricity, low-temperature operability, and copper strip corrosion.

"Controlling blending of the biofuel in response to the processor output signal" includes, but is not limited to, regulating the amount of cetane improver, antioxidant, or performance enhancer that is added to a biofuel, as well as controlling the amount of biodiesel, petroleum distillate, or petroleum-distillate-containing composition contained in a biodiesel blend or controlling the amount of a biodiesel blended with a jet fuel. Apparatus responsive to the processor output signal can be used to control blending, are well-known to those of ordinary skill in the art, and include, but are not limited to, process control devices and systems described hereinafter.

In certain aspects, the processor output signal may be transmitted electronically (e.g. wirelessly) from the processor to the apparatus or values indicative of the processor output signal may be entered into the apparatus manually or robotically using an appropriate interface.

Mass percentages of alkyl esters of fatty acids may be determined by any number of analyzers, e.g. a gas chromatograph, a gas chromatography microchip, a gas-liquid chromatography microchip, a micro-gas chromatograph (GC), a mass spectrophotometer, a gas chromatograph-mass spectrophotometer, a liquid chromatograph-mass spectrophotometer, an ion mobility spectrophotometer-mass spectrophotometer, an ultraviolet-visible (UV-Vis) absorbance spectrophotometer, an infrared (IR) absorbance spectrophotometer, a UV fluorescence spectrophotometer, a mid-infrared (MIR) absorbance spectrophotometer, a near infrared (NIR) absorbance spectrophotometer, a X-Ray fluorescence (XRF) spectrophotometer, a nuclear magnetic resonance spectrophotometer, a micro-oscillation spectrophotometer, micro-distillation-spectrophotometer, micro-mass spectrophotometer, or a micro-ion mobility spectrophotometer. In one aspect, the analyzer is gas chromatograph or a gas chromatography microchip and the mass percentages in the sample of the at least four methyl esters of fatty acids are determined in accordance with EN-14103.

Details on the preparation of biodiesel samples and conducting gas chromatography runs on such samples are provided in the ASTM D6584 standard. See Biodiesel Analytical Methods August 2002-January 2004, July 2004 NREL/SR-510-36240.

The total mass percentages of saturated, monounsaturated, and polyunsaturated fatty acid alkyl esters in the component are determined as follows. The total mass percentage of saturated fatty acid alkyl esters present in the component is determined by adding the mass percentages of those of the "at least two fatty acid alkyl esters" that are saturated fatty acid alkyl esters. The total mass percentage of monounsaturated fatty acid alkyl esters present in the component is determined by adding the mass percentages of those of the "at least two fatty acid alkyl esters" that are monounsaturated fatty acid alkyl esters. The total mass percentage of polyunsaturated fatty acid alkyl esters present in the component is determined by adding the mass percentages of those of the "at least two fatty acid alkyl esters" that are polyunsaturated fatty acid alkyl esters. The analyzer or processor can calculate such total mass percentages using hardware and software as described hereinafter or which is otherwise well-known to those of ordinary skill in the art.

"Ratios of the mass percentage of each of the at least two fatty acid alkyl esters and the total mass percentages of saturated, monounsaturated, and polyunsaturated fatty acid alkyl esters" are determined by dividing the mass percentage of each of the at least two fatty acid alkyl esters by (1) the mass percentage fatty acid alkyl esters (2) the mass percentage of monounsaturated fatty acid alkyl esters, and (3) the mass percentage of polyunsaturated fatty acid alkyl esters.

In certain aspects, "inputting values indicative of the at least two fatty acid alkyl ester mass percentages into a processor" includes transmitting a signal indicative of the fatty acid alkyl ester mass percentage measurements electronically (e.g. wirelessly) from the analyzer to the processor or entering the values into the processor manually or robotically using an appropriate interface. The analyzer and processor can be combined, e.g., the analyzer may include a processor as described herein. Values indicative of the total mass percentages of saturated, monounsaturated, and polyunsaturated fatty acid alkyl esters may be similarly inputted.

Algorithms useful in determining fatty acid alkyl ester volumetric percentages may be derived from a statistical correlation of the determined ratios of the mass percentages of alkyl esters of fatty acids, or the determined ratios of the mass percentages of alkyl esters of fatty acids and the total mass percentages of fatty acid alkyl esters using a variety of statistical techniques. For example, principle component analysis/regression (PCA/PCR), partial least squares (PLS), and Gauss-Jordan row reduction may be used to derive algorithms that predict volumetric percentages of the various vegetable and animal alkyl esters based on determined ratios of the mass percentages of alkyl esters of fatty acids.

Artificial neural network techniques which have been used to model biodiesel manufacturing conditions and physical properties, see Rajendra, et al., "Prediction of optimized pretreatment process parameters for biodiesel production using ANN and GA", Fuel. Vol. 88, Issue 5 May 2009, pp. 868-875, Baroutian, et al., "Predication of Palm Oil-Based Methyl Ester Biodiesel Density Using Artificial Neural Networks", *Journal of Applied Sciences* 8(10): 1938-1943, 2008, may be adapted to derive the requisite algorithms through principles well-known to those of ordinary skill in the art.

Alternatively, through programming techniques well-known to those of ordinary skill in the art, neural network may use associative memory to correlate fatty acid alkyl ester mass percentage ratios and volumetric percentages.

Algorithms may be adjusted or confirmed as necessary by analyzing a sample of a fatty acid alkyl ester-containing biofuel to determine, e.g., the volumetric percentages of vegetable and animal oil fatty acid esters, comparing determined volumetric percentages with corresponding algorithmically-predicted volumetric percentages, and revising the algorithm through one or more of the mathematical techniques described above if differences between determined volumetric percentages and corresponding algorithmically-predicted volumetric percentages exceed an acceptable tolerance.

As used herein the terms "predict" and "determine" are meant generally to encompass techniques or algorithms whose measurements or output fall within an acceptable range of error when compared to standardized methods (e.g., ASTM) of measuring the same property. An acceptable range of error may be within 15 percent, preferably within 10 percent, and more preferably 5 percent or less of the value measured by standardized methods (e.g., ASTM). Thus, where one measuring technique or algorithm has a range of error in excess of 15 percent of a standardized method, such a technique or algorithm would not be considered to be predictive or determinative of the property sought to be measured or otherwise ascertained. In contrast, where another measuring technique or algorithm has a range of error of 15 percent or less, then such a technique or algorithm would be considered to be predictive or determinative of the property sought to be measured or otherwise ascertained.

A programmable logic controller may be used as the processor which calculates the ratios of the mass percentages of the fatty acid alkyl esters and total mass percentages of saturated, monounsaturated, and polyunsaturated fatty acid alkyl esters and which performs one or more algorithms that determine fatty acid alkyl ester volumetric percentages. Programmable controllers are well-known to those of ordinary skill in the art and receive process inputs and adjust process parameters based on such inputs. Programmable controllers include but are not limited to electronic programmable logic controllers (PLC's) and personal computers. Useful programmable logic controllers can include computer systems comprising central processing units (CPU's) for processing data, associated memory media including floppy disks or compact discs (CD's) which may store program instructions for CPU's, one or more display devices such as monitors, one or more alphanumeric input devices such as a keyboard, and one or more directional input devices such as a mouse. Computer systems used as programmable logic controls can include a computational system memory such as DRAM, SRAM, EDO DRAM, SDRAM, DDR SDRAM, or Rambus RAM, or a non-volatile memory such as a magnetic media (e.g., a hard drive) or optical storage. The memory medium preferably stores a software program or programs for event-triggered transaction processing. The software program(s) may be implemented in any of various ways, including procedure-based techniques, component-based techniques, and/or object-oriented techniques, among others.

Programmable controllers (e.g., PLC's) can, through hardwire or wireless transmission techniques that are well-known to those of ordinary skill in the art, may receive data, e.g. from apparatus that determine mass percentages of alkyl esters of fatty acids in a biodiesel feedstock sample, in order to implement the procedures described herein, e.g., to control the mixing of the biodiesel and the one or more additional components.

Portions of the methods described herein can be applied as open loop or closed loop systems. Conventional PID (Proportional-Integrated-Derivative) controllers, DCS (distributed control systems), and other traditional control systems such as ratio controls and feed-forward controls can be applied to implement the methods described herein.

Programmable logic controllers in the form of computer systems may take various forms, including a personal computer system, mainframe computer system, workstation, network appliance, Internet appliance or other device and encompass any device (or collection of devices) having a processor (or processors) which executes instructions from a memory medium.

A memory medium (which may include a plurality of memory media) can store one or more software programs for performing various aspects of the methods that are predictive and used in control and optimization. The software program (s) can be implemented using component-based techniques and/or object-oriented techniques. For example, the software program may be implemented using ActiveX controls, C++ objects, Java objects, Microsoft Foundation Classes (MFC), or other technologies or methodologies, as desired. A CPU, such as the host CPU, executing code and data from the memory medium comprises a means for creating and executing the software program according to the methods described herein. In some embodiments, one or more computer systems may implement one or more controllers.

In one aspect, the methods described herein provide a method of optimizing the composition of a fuel comprising a mixture of a biodiesel or biodiesel blend and one or more additional components in which:

(a) the mass percentages of methyl esters of palmitic acid (C16:0), palmitoleic acid (C16:1), oleic acid (C18:1), and linoleic acid (C18:2) in the biodiesel or biodiesel component of a biodiesel blend are measured using a gas chromatograph, a gas chromatography microchip, a gas-liquid chromatography microchip, a micro-gas chromatograph (GC), a mass spectrophotometer, a gas chromatograph-mass spectrophotometer, a liquid chromatograph-mass spectrophotometer, an ion mobility spectrophotometer-mass spectrophotometer, an ultraviolet-visible (UV-Vis) absorbance spectrophotometer, an infrared (IR) absorbance spectrophotometer, a UV fluorescence spectrophotometer, a mid-infrared (MIR) absorbance spectrophotometer, a near infrared (NIR) absorbance spectrophotometer, a X-Ray fluorescence (XRF) spectrophotometer, a nuclear magnetic resonance spectrophotometer, a micro-oscillation spectrophotometer, micro-distillation-spectrophotometer, micro-mass spectrophotometer, or a micro-ion mobility spectrophotometer;(b) the fatty acid alkyl ester mass percentage measurements are transmitted to a programmable logic controller which:

(1) calculates the following mass percentages ratios: (i) linoleic acid methyl ester: oleic acid methyl ester; (ii) oleic acid methyl ester: palmitic acid methyl ester; (iii) palmitoleic acid methyl ester: palmitic acid methyl ester; and (iv) palmitic acid methyl ester: oleic acid methyl ester;

(2) performs the following algorithms to determine the volumetric percentages of soybean oil methyl ester (SME), rapeseed oil methyl ester (RME), tallow oil methyl ester (TME), and palm oil methyl ester (PME) in the biodiesel or biodiesel component of a biodiesel blend:

(a) SME=$0.993*(C18:2 \text{ cis-9, } 12/C18:1 \text{ cis-9})^{0.5}-0.520$;
(b) RME=$0.089*(C18:1 \text{ cis-9}/C16:0)-0.104$;
(c) TME=$86.671*(C16:1 \text{ cis-9}/C16:0)^2-0.030$; and
(d) PME=$0.018*(C16:0/C18:1 \text{ trans-9})-0.069$;

(3) correlates the volumetric percentages of soybean oil methyl ester (SME), rapeseed oil methyl ester (RME), tallow oil methyl ester (TME), and palm oil methyl ester (PME) with programmed values for fuel performance data selected from the group consisting of lubricity, specific gravity, kinematic viscosity, flash point, boiling point, cetane number, cloud point, pour point, lubricity, and copper strip corrosion and generates an output signal indicative of that correlation;

(4) controls mixing of the biodiesel or biodiesel blend and one or more additional components selected from the group consisting of a petroleum distillate, a cetane improver, a performance additive, and an antioxidant in response to the processor output signal; and optionally (5) correlates the volumetric percentages of soybean oil methyl ester (SME), rapeseed oil methyl ester (RME), tallow oil methyl ester (TME), and palm oil methyl ester (PME) to reference biodiesel feedstock triglyceride profiles and determines the biodiesel's feedstock.

Those of ordinary skill in the art will appreciate that methods of the invention can be applied using a variety of well-known equipment and process control schemes.

These and other aspects of the invention are illustrated by the following example, which is illustrative only and is not limiting.

EXAMPLE 1

Figure 1:
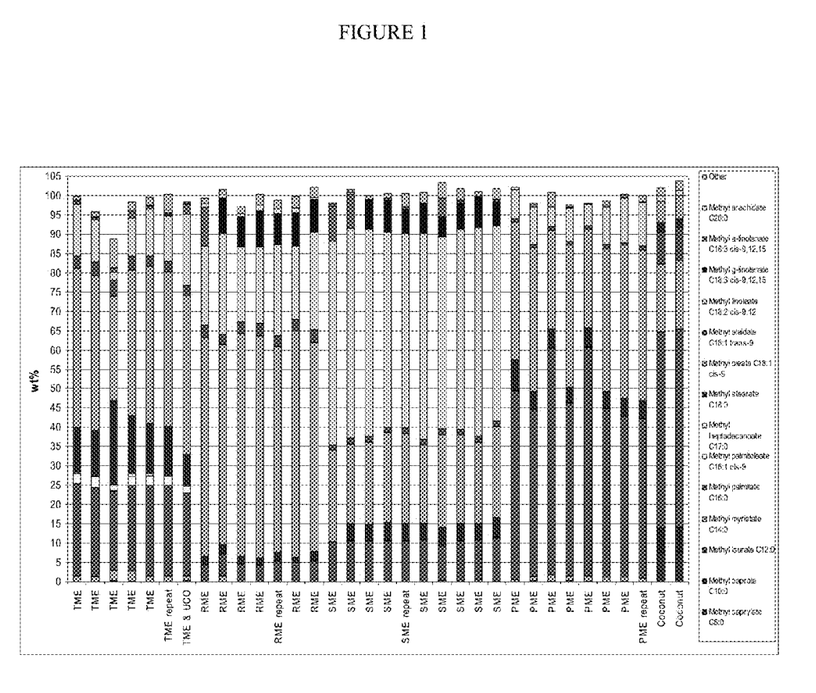
FIG. 1 and FIG. 2 illustrate gas chromatographic analyses of the fatty acid alkyl ester profiles of vegetable and animal oil fatty acid alkyl esters, as determined or described in the experiment of Example 1 and Example 2, respectively. The gas chromatograph data in FIG. 1 is raw and the gas chromatograph data in FIG. 2 is normalized.

The fatty acid methyl ester (FAME) profiles of thirty biodiesel samples were analyzed by gas chromatography. The resultant analyses of biodiesel composition by feedstock type were entered into a database and are presented in FIG. 1.

The following components were used to prepare Blends #1 through #8 below:
Soybean Methyl Ester (SME)—Code #06-23754
Rapeseed Methyl Ester (RME)—Code #06-24237
Tallow Methyl Ester (TME)—Code #06-23646
Palm Oil Methyl Ester (PME)—Code #07-17170
ULSD—Code #03-57259.

The following blends were prepared.
Blend #1 SME/RME/TME/PME (25/75/0/0 vol %)
Blend #2 SME/RME/TME/PME (50/50/0/0 vol %)
Blend #3 SME/RME/TME/PME (75/25/0/0 vol %)
Blend #4 SME/RME/TME/PME (25/25/25/25 vol %)
Blend #5 SME/RME/TME/PME (40/30/20/10 vol %)
Blend #6 ULSD/SME (80/20 vol %)
Blend #7 ULSD/Blend #2 (80/20 vol %) (composition of the
  biodiesel being SME/RME/TME/PME (10/10/0/0 vol %)
Blend #8 ULSD/Blend #4 (80/20 vol %) (composition of the
  biodiesel being SME/RME/TME/PME (5/5/5/5 vol %)

The blends were analyzed by gas chromatography. For the biodiesel samples in the database and Blends #1 through #5 above, the ratios of the different methyl esters in each sample were calculated. This data was entered into a regression program (XLSTAT (Addinsoft, New York, N.Y.)) and were used to generate the following prediction equations:

(a) SME=0.993*(C18:2 cis-9, 12/C18:1 cis-9)0.5−0.520
(b) RME=0.089*(C18:1 cis-9/C16:0)−0.104;
(c) TME=86.671*(C16:1 cis-9/C16:0)2−0.030; and
(d) PME=0.018*(C16:0/C18:1 trans-9)−0.069.

These equations were then used to predict the biodiesel feedstock composition of Blends #1 through #8. The results, normalized to 100 volume %, are reported below.
Blend #1 SME/RME/TME/PME(27/66/7/0 vol %)
Blend #2 SME/RME/TME/PME (52/46/2/0 vol %)
Blend #3 SME/RME/TME/PME (73/25/0/2 vol %)
Blend #4 SME/RME/TME/PME (51/10/13/26 vol %)
Blend #5 SME/RME/TME/PME (54/18/20/8 vol %)
Blend #6 SME/RME/TME/PME (18.3/1.4/0/0.3 vol %)
Blend #7 SME/RME/TME/PME (10/9.8/0.6/0 vol %)
Blend #8 SME/RME/TME/PME (10.8/2.2/2.6/4.4 vol %)

The predicted fatty acid alkyl ester profiles of the biodiesels or biodiesel components of the biodiesel blends agreed very well with the actual fatty acid alkyl ester profiles of the biodiesels and biodiesel components of the biodiesel blends.

EXAMPLE 2

Figure 2:
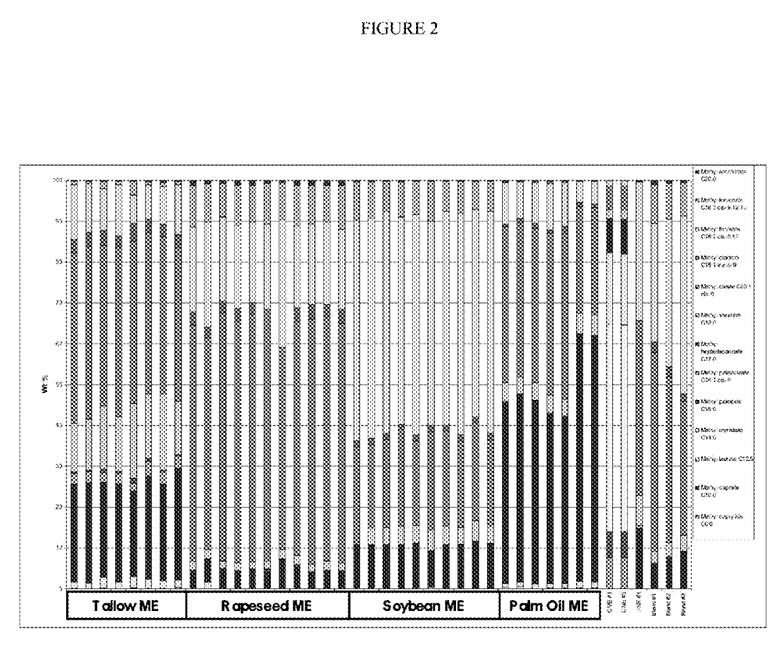

The fatty acid methyl ester (FAME) profiles of forty two biodiesel samples were analyzed by gas chromatography. The resultant analyses of biodiesel composition by feedstock type were normalized and entered into a database and are presented in FIG. 2.

Figure 3D:
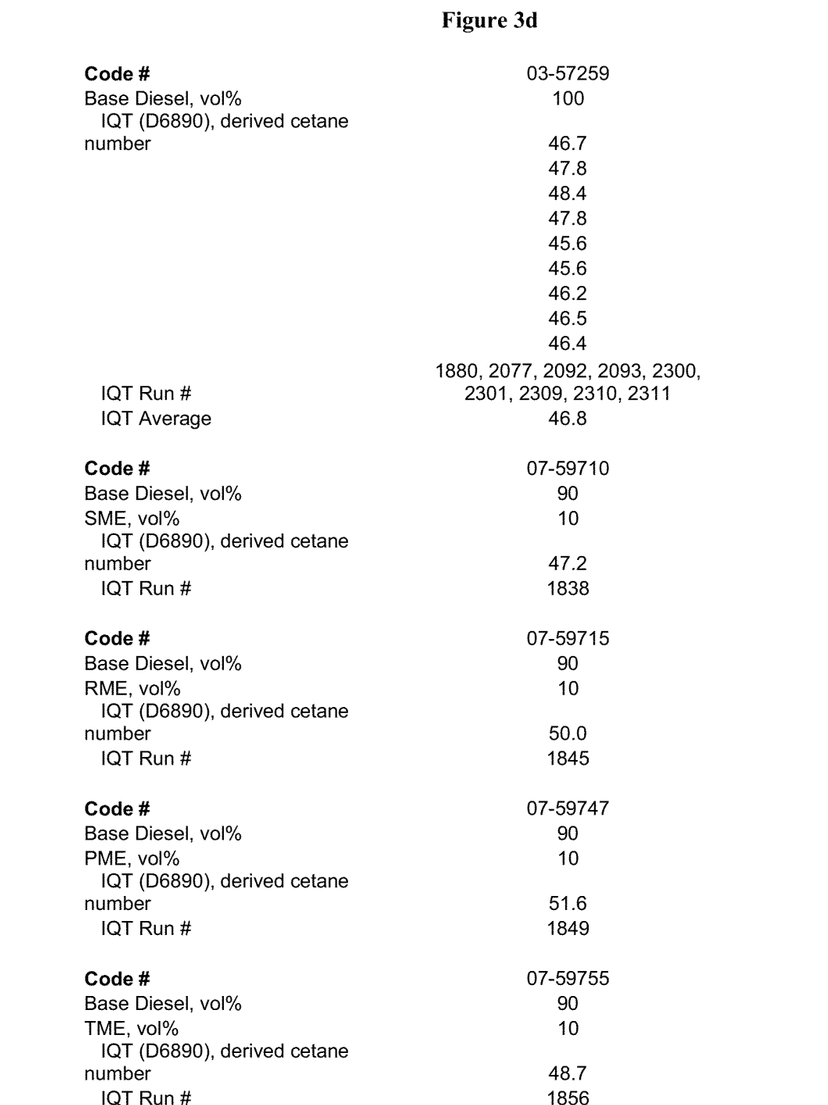
FIG. 3d is the IQT data determined in Example 2.

FIGS. 3a, 3b, 3c and 3d present the fuel composition, fuel properties, and fuel fatty acid alkyl ester profile determined in Example 2. FIG. 3a presents the base diesel fuel properties determined in Example 2. FIG. 3b is the FAME Composition Calculator (fuel fatty acid alkyl ester profile) determined in Example 2. FIG. 3c is the GC analysis of biodiesel samples determined in Example 2. FIG. 3d is the IQT data determined in Example 2.

To a base diesel fuel (with an ASTM D6890 derived cetane number of 46.8; FIG. 3a) was added 10 vol % of a B100 sample (determined algorithmically (FIG. 3c) to comprise mostly PME). The resultant blend had an ASTM D6890 derived cetane number of 51.6. The following algorithms were used:

(a) TME=−0.053+0.219*(C16:1 cis-9)+0.039*(C16:1 cis-9 to C20:0)
(b) RME=−0.149+0.079*(C18:1 cis-9 to sats)+0.019*(C18:1 cis-9 to C18:0)
(c) SME=−0.133+0.476*(C18:2 cis-9,12 to C18:1 cis-9)
(d) PME=−0.258+0.005*(C16:0)+0.094*(C16:0 to C18:0)
(e) CME=2.244E-8+0.835*(C8:0 to C10:0)
(f) JME=−2.034E-3*(C18:1 cis-9 to C18:3 cis-9,12,15)+0.035*(C18:2 cis-9,12 to C18:3 cis-9,12,15)−0.026*(poly to C18:3 cis-9,12,15)

The U.S. (ASTM D975) and European (EN590) diesel fuel specifications differ with regard to cetane number. The D975 specification is 40 min compared to the EN590 specification of 51.0 min. Accordingly, consistent with fuel properties expected from the algorithmic determination of B100 fatty acid alkyl ester composition, blending of the B100 with the diesel yielded a fuel which satisfied EN590.

It is to be understood that the above description is intended for illustrative purposes only, and is not intended to limit the scope of the present invention in any way.

It is to be understood that the above description is intended for illustrative purposes only and is not intended to limit the scope of the present invention in any way.

What is claimed is:

1. A method of optimizing the composition of a biofuel comprised of fatty acid alkyl esters, the method comprising:
 (a) submitting a sample of a fatty acid alkyl ester-containing component of the biofuel to an analyzer which measures the mass percentages in the component of at least two fatty acid alkyl esters;
 (b) inputting values indicative of the at least two fatty acid alkyl ester mass percentages into a processor which, in accordance with preprogrammed instructions, (1) calculates one or more fatty acid alkyl ester mass percentage ratios and algorithmically determines the volumetric percentages of one or more fatty acid alkyl esters in the component using the one or more fatty acid alkyl ester mass percentage ratios as algorithmic independent variables, and (2) correlates the one or more fatty acid alkyl ester volumetric percentages to fuel performance data and generates an output signal indicative of that correlation; and (c) controlling blending of the biofuel in response to the processor output signal.

2. The method of claim 1, wherein the analyzer measures mass percentages of four or more fatty acid alkyl esters in step (a), such that the mass percentages are input in step (b) into the processor, which then calculates four or more fatty acid alkyl ester mass percentage ratios and algorithmically determines the volumetric percentages of four or more fatty acid alkyl esters.

3. The method of claim 1, wherein:
(a) the analyzer is gas chromatograph, a gas chromatography microchip, a gas-liquid chromatography microchip, a micro-gas chromatograph (GC), a mass spectrophotometer, a gas chromatograph-mass spectrophotometer, a liquid chromatograph- mass spectrophotometer, an ion mobility spectrophotometer-mass spectrophotometer, an ultraviolet-visible (UV-Vis) absorbance spectrophotometer, an infrared (IR) absorbance spectrophotometer, a UV fluorescence spectrophotometer, a mid-infrared (MIR) absorbance spectrophotometer, a near infrared (NIR) absorbance spectrophotometer, a X-Ray fluorescence (XRF) spectrophotometer, a nuclear magnetic resonance spectrophotometer, a micro-oscillation spectrophotometer, micro-distillation-spectrophotometer, micro-mass spectrophotometer, or a micro-ion mobility spectrophotometer; and
(b) the processor is a programmable logic controller.

4. The method of claim 1, wherein the biofuel is a biodiesel or a biodiesel blend and the volumetric percentages of one or more fatty acid alkyl esters are correlated to reference biodiesel feedstock triglyceride profiles and the biodiesel's feedstock, or the feedstock of the biodiesel component of the biodiesel blend, is thereby determined.

5. The method of claim 1, wherein the biofuel is a jet biofuel comprised of fatty acid alky esters.

6. The method of claim 1, wherein the fuel performance data represents values indicative of properties selected from the group consisting of lubricity, specific gravity, kinematic viscosity, flash point, boiling point, cetane number, cloud point, pour point, lubricity, and copper strip corrosion.

7. The method of claim 1, wherein the biofuel is a biodiesel or biodiesel blend and the processor determines the volumetric percentage of one or more compositions selected from the group consisting of soybean oil alkyl ester, rapeseed oil alkyl ester, palm oil alkyl ester, canola oil alkyl ester, sunflower oil alkyl ester, olive oil alkyl ester, corn oil alkyl ester, tallow oil alkyl ester, coconut oil alkyl ester, jatropha oil alkyl ester, yellow grease alkyl ester, animal fat alkyl ester, and used cooking oil alkyl ester.

8. The method of claim 1, wherein the biofuel is a biodiesel or biodiesel blend and the analyzer measures the mass percentages of at least four alkyl esters of fatty acids selected from the group consisting of myristic acid (C14:0), palmitic acid (C16:0), palmitoleic acid (C16:1), stearic acid (C18:0), oleic acid (C18:1), linoleic acid (C18:2), linolenic acid (C18:3), eicosanoic acid (C20:0), eicosenoic acid (C20:1), docosanoic acid (C22:0), and docosenoic acid (C22:1).

9. The method of claim 1, wherein the method further comprises:
(a) determining total mass percentages of saturated, monounsaturated, and polyunsaturated fatty acid alkyl esters in the component; and
(b) inputting values indicative of the total mass percentages of saturated, monounsaturated, and polyunsaturated fatty acid alkyl esters into the processor which, in accordance with preprogrammed instructions (1) calculates (i) one or more fatty acid alkyl ester mass percentage ratios (ii) ratios of the mass percentage of each of the at least two fatty acid alkyl esters and the total mass percentages of saturated, monounsaturated, and polyunsaturated fatty acid alkyl esters (2) algorithmically determines the volumetric percentages of one or more fatty acid alkyl esters in the component using the one or more fatty acid alkyl ester mass percentage ratios, the total mass percentages of saturated, monounsaturated, and polyunsaturated fatty acid alkyl esters, and ratios of the mass percentage of each of the at least two fatty acid alkyl esters and the total mass percentages of saturated, monounsaturated, and polyunsaturated fatty acid alkyl esters as algorithmic independent variables.

10. The method of claim 1, wherein the analyzer not only measures the mass percentages in the component of at least two fatty acid alkyl esters in step (a), but also contains the processor and is adapted to automatically input the measured values from step (a) into the processor according to step (b).

11. The method of claim 1, wherein one of or more compositions selected from the group consisting of a petroleum distillate, a cetane improver, a performance additive, and an antioxidant are blended with the biofuel in response to the processor output signal.

12. The method of claim 11, wherein:
(a) the cetane improver is selected from the group consisting of 2-ethylhexyl nitrate, cyclohexyl nitrate, di-tert-butyl peroxide, methyl nitrate, ethyl nitrate, n-propyl nitrate, isopropyl nitrate, allyl nitrate, n-butyl nitrate, isobutyl nitrate, sec-butyl nitrate, tert-butyl nitrate, n-amyl nitrate, isoamyl nitrate, 2-amyl nitrate, 3-amyl nitrate, tert-amyl nitrate, n-hexyl nitrate, 2-ethylhexyl nitrate, n-heptyl nitrate, sec-heptyl nitrate, n-octyl nitrate, sec-octyl nitrate, n-nonyl nitrate, n-decyl nitrate, n-dodecyl nitrate, cyclopentylnitrate, cyclohexylnitrate, methylcyclohexyl nitrate, isopropylcyclohexyl nitrate, 1-methoxypropyl-2-nitrate, 1-ethoxpropyl-2 nitrate, 1-isopropoxy-butyl nitrate, 1-ethoxylbutyl nitrate, and mixtures thereof
(b) the performance enhancer is selected from the group consisting of cold flow additives, cloud point depressants, biocides, conductivity improvers, corrosion inhibitors, metal deactivators, engine cleaning agents, and mixtures thereof; and
(c) the antioxidant is selected from the group consisting of amine-based antioxidants, phenolic antioxidants, sulfur-based antioxidants, phosphorous-based antioxidants, zinc dithiophosphate, oil-soluble copper compounds, and mixtures thereof.

13. The method of claim 12, wherein:
(a) the biofuel is a biodiesel or biodiesel blend;
(b) the analyzer measures the mass percentages of methyl esters of palmitic acid (C16:0), palmitoleic acid (C16:1), oleic acid (C18:1), and linoleic acid (C18:2);
(c) the processor calculates the following mass percentage ratios: (1) linoleic acid methyl ester: oleic acid methyl ester; (2) oleic acid methyl ester: palmitic acid methyl ester; (3) palmitoleic acid methyl ester: palmitic acid methyl ester; and (4) palmitic acid methyl ester: oleic acid methyl ester; and
(d) the processor determines the volumetric percentage of: (1) soybean oil methyl ester; (2) rapeseed oil methyl ester; (3) tallow oil methyl ester; and (4) palm oil methyl ester.

14. The method of claim 13, wherein
(a) the linoleic acid (C18:2) is linoleic acid (C18:2 cis 9, 12); and (b) the oleic acid (C18:1) is either oleic acid (C18:1 cis 9) or oleic acid (C18:1 trans 9).

15. The method of claim 14, wherein the processor determines the volumetric percentage of soybean oil methyl ester (SME), rapeseed oil methyl ester (RME), tallow oil methyl ester (TME), palm oil methyl ester (PME), coconut oil methyl ester (CME), and jatropha oil methyl ester (JME) using either or both of the following two sets of algorithms:

Set 1
(a) $SME=0.993*(C18:2\ cis-9, 12/C18:1\ cis-9)^{0.5}-0.520$;
(b) $RME=0.089*(C18:1\ cis-9/C16:0)-0.104$;
(c) $TME=86.671*(C16:1\ cis-9/C16:0)^2-0.030$; and
(d) $PME=0.018*(C16:0/C18:1\ trans-9)-0.069$ Set 2
(a) $TME=-0.053+0.219*(C16:1\ cis-9)+0.039*(C16:1\ cis-9\ to\ C20:0)$
(b) $RME=-0.149+0.079*(C18:1\ cis-9\ to\ sats)+0.019*(C18:1\ cis-9\ to\ C18:0)$
(c) $SME=-0.133+0.476*(C18:2\ cis-9,12\ to\ C18:1\ cis-9)$
(d) $PME=-0.258+0.005*(C16:0)+0.094*(C16:0\ to\ C18:0)$
(e) $CME=2.244E-8+0.835*(C8:0\ to\ C10:0)$
(f) $JME=-2.034E-3*(C18:1\ cis-9\ to\ C18:3\ cis-9,12,15)+0.035*(C18:2\ cis-9,12\ to\ C18:3\ cis-9,12,15)-0.026*(poly\ to\ C18:3\ cis-9,12,15)$.

16. The method of claim 15, wherein:
(a) the fuel performance data represents values indicative of properties selected from the group consisting of lubricity, specific gravity, kinematic viscosity, flash point, boiling point, cetane number, cloud point, pour point, lubricity, and copper strip corrosion; and
(b) blending of the biofuel and one or more additional compositions selected from the group consisting of a petroleum distillate, a cetane improver, a performance additive, and an antioxidant is controlled in response to the output signal.

17. The method of claim 16, wherein:
(a) the analyzer is gas chromatograph, a gas chromatography microchip, a gas-liquid chromatography microchip, a micro-gas chromatograph (GC), a mass spectrophotometer, a gas chromatograph -mass spectrophotometer, a liquid chromatograph- mass spectrophotometer, an ion mobility spectrophotometer - mass spectrophotometer, an ultraviolet-visible (UV-Vis) absorbance spectrophotometer, an infrared (IR) absorbance spectrophotometer, a UV fluorescence spectrophotometer, a mid-infrared (MIR) absorbance spectrophotometer, a near infrared (NIR) absorbance spectrophotometer, a X-Ray fluorescence (XRF) spectrophotometer, a nuclear magnetic resonance spectrophotometer, a micro-oscillation spectrophotometer, micro-distillation-spectrophotometer, micro-mass spectrophotometer, or a micro-ion mobility spectrometry; and
(b) the processor is a programmable logic controller.

18. The method of claim 17, wherein the biofuel is a biodiesel blend that comprises about 2% to about 98% by volume of a biodiesel and about 2% to about 98% by volume of a petroleum distillate.

19. A method of optimizing the composition of a biofuel comprised of fatty acid alkyl esters, the method comprising:
(a) submitting a sample of a fatty acid alkyl ester-containing component of the biofuel to an analyzer which measures the mass percentages in the component of at least two fatty acid alkyl esters;
(b) inputting values indicative of the at least two fatty acid alkyl ester mass percentages into a processor which (1) calculates one or more fatty acid alkyl ester mass percentage ratios and algorithmically determines the volumetric percentages of one or more fatty acid alkyl esters in the component using the one or more fatty acid alkyl ester mass percentage ratios as algorithmic independent variables (2) correlates the one or more fatty acid alkyl ester volumetric percentages to fuel performance data and generates an output signal indicative of that correlation; and
(c) controlling blending of the biofuel in response to the processor output signal, wherein the processor is a neural network which uses associative memory to generate algorithms that determine the volumetric percentages of one or more fatty acid alkyl esters.

20. The method of claim 19, wherein the method further comprises:
(a) determining total mass percentages of saturated, monounsaturated, and polyunsaturated fatty acid alkyl esters in the component; and
(b) inputting values indicative of the total mass percentages of saturated, monounsaturated, and polyunsaturated fatty acid alkyl esters into the processor which calculates one or more fatty acid alkyl ester mass percentage ratios and algorithmically determines the volumetric percentages of one or more fatty acid alkyl esters in the component using the one or more fatty acid alkyl ester mass percentage ratios, the total mass percentages of saturated, monounsaturated, and polyunsaturated fatty acid alkyl esters, and and ratios of the mass percentage of each of the at least two fatty acid alkyl esters and the total mass percentages of saturated, monounsaturated, and polyunsaturated fatty acid alkyl esters as algorithmic independent variables.

* * * * *